(12) United States Patent
Elliott et al.

(10) Patent No.: US 10,893,856 B2
(45) Date of Patent: Jan. 19, 2021

(54) WOUND CLOSURE PRODUCT

(71) Applicant: Wound Care Technologies, Inc., Chanhassen, MN (US)

(72) Inventors: Daniel M. Elliott, Shorewood, MN (US); George M. Hoedeman, Eden Prairie, MN (US); John J. Berkey, Buffalo, MN (US); Paul J. Anderson, Eden Prairie, MN (US); Robert C. Wilke, Eden Prairie, MN (US)

(73) Assignee: Wound Care Technologies, Inc., Chanhassen, MN (US)

( * ) Notice: Subject to any disclaimer, the term of this patent is extended or adjusted under 35 U.S.C. 154(b) by 509 days.

(21) Appl. No.: 15/426,376

(22) Filed: Feb. 7, 2017

(65) Prior Publication Data

US 2017/0238932 A1 Aug. 24, 2017

Related U.S. Application Data

(63) Continuation of application No. 14/511,416, filed on Oct. 10, 2014, now Pat. No. 9,597,079, which is a
(Continued)

(51) Int. Cl.
*A61B 17/04* (2006.01)

(52) U.S. Cl.
CPC .. *A61B 17/0401* (2013.01); *A61B 2017/0412* (2013.01); *A61B 2017/0496* (2013.01)

(58) Field of Classification Search
CPC ............. A61B 17/08; A61B 17/0401; A61B 17/06166; A61B 2017/081;
(Continued)

(56) References Cited

U.S. PATENT DOCUMENTS 114,750 A 5/1871 Battersby
363,538 A 5/1887 Penny
(Continued)

FOREIGN PATENT DOCUMENTS

EP 0 531 742 A1 3/1993
FR 2 268 504 11/1975
(Continued)

OTHER PUBLICATIONS

Canica® design brochure, "Canica Wound Closure System," © Canica Design, 2004 (5 pages).
(Continued)

*Primary Examiner* — Dianne Dornbusch
(74) *Attorney, Agent, or Firm* — K&L Gates LLP

(57) ABSTRACT

A wound closure system and a method of closing a wound are disclosed. The disclosure is directed to a wound closure system comprising a skin anchor mechanically attached to external skin tissue on a first side of a generally linear wound, an anchorable tensioning apparatus mechanically attached to external skin tissue on an opposite side of the wound, and a line extending between the skin anchor and the tensioning apparatus to movably connect the anchor to the tensioning apparatus. The line is fixedly engaged with an anchor on one side of the wound while the tensioning apparatus provides tension on the line to draw the skin anchor and the tensioning apparatus toward each other and toward the wound.

13 Claims, 5 Drawing Sheets

Related U.S. Application Data continuation of application No. 12/750,353, filed on Mar. 30, 2010, now Pat. No. 8,864,796, which is a continuation of application No. 10/982,509, filed on Nov. 4, 2004, now Pat. No. 7,686,829.

(58) Field of Classification Search
CPC ........ A61B 17/0466; A61B 2017/0496; A61B 2017/088; A61B 90/02; A61B 2017/0412; A43C 11/165
See application file for complete search history.

(56) References Cited

U.S. PATENT DOCUMENTS

| | | | |
|---|---|---|---|
| 2,421,193 A | 5/1947 | Gardner | |
| 3,402,716 A | 9/1968 | Baxter | |
| 3,559,652 A | 2/1971 | Banitt et al. | |
| 3,650,274 A * | 3/1972 | Edwards | A61B 17/0466 606/233 |
| 3,825,010 A | 7/1974 | McDonald | |
| 3,959,960 A * | 6/1976 | Santos | A61B 17/04 606/82 |
| 4,646,731 A | 3/1987 | Brower | |
| 4,742,826 A | 5/1988 | McLorg | |
| 4,825,866 A | 5/1989 | Pierce | |
| 4,901,938 A * | 2/1990 | Cantley | B65H 75/44 242/378.1 |
| 5,108,433 A * | 4/1992 | May | A61F 2/0811 606/90 |
| 5,127,412 A | 7/1992 | Cosmetto et al. | |
| 5,234,462 A * | 8/1993 | Pavletic | A61B 17/085 606/215 |
| 5,330,489 A | 7/1994 | Green et al. | |
| 5,356,412 A | 10/1994 | Golds et al. | |
| 5,411,222 A * | 5/1995 | Gray | B60R 22/44 242/375.3 |
| 5,422,957 A * | 6/1995 | Cummins | B65H 75/4431 381/384 |
| 5,433,648 A * | 7/1995 | Frydman | A41C 3/0028 2/183 |
| 5,462,542 A | 10/1995 | Alesi, Jr. | |
| 5,486,196 A * | 1/1996 | Hirshowitz | A61B 17/08 606/150 |
| 5,507,775 A | 4/1996 | Ger et al. | |
| 5,556,428 A * | 9/1996 | Shah | A61B 17/1146 606/151 |
| 5,582,585 A * | 12/1996 | Nash-Morgan | A45D 44/22 428/343 |
| 5,618,310 A | 4/1997 | Ger et al. | |
| 5,649,960 A * | 7/1997 | Pavletic | A61B 17/085 606/215 |
| 5,746,192 A * | 5/1998 | Gissel | F41B 5/14 124/1 |
| 5,762,281 A * | 6/1998 | Foley | B65H 75/28 160/178.1 R |
| 5,769,893 A | 6/1998 | Shah | |
| 5,843,123 A | 12/1998 | Brazeau | |
| 5,893,879 A * | 4/1999 | Hirshowitz | A61B 17/08 606/213 |
| 5,968,097 A | 10/1999 | Frechet et al. | |
| 5,980,473 A | 11/1999 | Korakianitis et al. | |
| 6,120,525 A * | 9/2000 | Westcott | A61B 17/0466 606/216 |
| 6,182,335 B1 * | 2/2001 | Juda | A47G 21/165 24/115 H |
| 6,199,785 B1 * | 3/2001 | Paugh | B65H 75/4431 242/378.1 |
| 6,213,421 B1 * | 4/2001 | Franklin | B60C 27/066 152/219 |
| 6,241,747 B1 | 6/2001 | Ruff | |
| 6,254,624 B1 * | 7/2001 | Oddsen | A61B 17/08 606/150 |
| 6,421,044 B2 * | 7/2002 | Murphy | G06F 3/039 345/163 |
| 6,471,715 B1 * | 10/2002 | Weiss | A61B 17/04 606/216 |
| 6,599,310 B2 | 7/2003 | Leung et al. | |
| 6,613,059 B2 | 9/2003 | Schaller et al. | |
| 6,619,353 B1 * | 9/2003 | Kim | B60C 27/02 152/218 |
| 6,871,812 B1 * | 3/2005 | Chang | B65H 75/4434 191/12.4 |
| 6,960,221 B2 | 11/2005 | Ho et al. | |
| 7,056,331 B2 | 6/2006 | Kaplan et al. | |
| 7,208,006 B2 * | 4/2007 | Fleischmann | A61B 90/02 606/216 |
| 7,455,681 B2 | 11/2008 | Wilke et al. | |
| 7,686,829 B2 | 3/2010 | Wilke et al. | |
| 7,927,352 B2 | 4/2011 | Wilke et al. | |
| 7,972,362 B2 | 7/2011 | Wilke et al. | |
| 2001/0018592 A1 | 8/2001 | Schaller et al. | |
| 2001/0047181 A1 | 11/2001 | Ho et al. | |
| 2003/0073979 A1 * | 4/2003 | Naimark | A61B 17/00234 604/891.1 |
| 2003/0092969 A1 * | 5/2003 | O'Malley | A61B 17/02 600/216 |
| 2003/0149447 A1 | 8/2003 | Morency | |
| 2003/0163160 A1 * | 8/2003 | O'Malley | A61B 17/08 606/213 |
| 2005/0081339 A1 * | 4/2005 | Sakabayashi | A43C 7/00 24/128 |
| 2005/0085851 A1 * | 4/2005 | Fiehler | A61B 17/0057 606/213 |
| 2005/0131430 A1 | 6/2005 | Ravidumar | |
| 2005/0184186 A1 * | 8/2005 | Tsoi | B65H 75/4431 242/378.1 |
| 2005/0192599 A1 | 9/2005 | Demarias | |
| 2006/0058842 A1 * | 3/2006 | Wilke | A61B 17/0466 606/213 |
| 2006/0095076 A1 | 5/2006 | Elliott et al. | |
| 2008/0097483 A1 | 4/2008 | Ortiz et al. | |
| 2009/0018578 A1 | 1/2009 | Wilke et al. | |
| 2009/0018579 A1 | 1/2009 | Wilke et al. | |
| 2010/0185236 A1 | 7/2010 | Elliott et al. | |

FOREIGN PATENT DOCUMENTS

| | | |
|---|---|---|
| WO | WO 95/28886 | 11/1995 |
| WO | WO 99/35974 | 7/1999 |
| WO | WO 2005/002452 | 1/2005 |
| WO | WO 2005/016153 | 2/2005 |

OTHER PUBLICATIONS

Topical Hyperbaric Oxygen™ Therapy, "Healing Difficult Wounds," http://www.gwrmedical.com, 3 pages (date printed: Apr. 28, 2004).
Progressive Surgical Products Inc. brochure, "External Tissue Expansion," Proxiderm™, Copyright 1997 (3 pages).
"History of Wound Care," http://www.proxiderm.com/html/intro2.html, 3 pages (date printed: Jul. 28, 2004).
"Proxiderm Procedure," http://www.proxiderm.com/html/intro3.html, 2 pages (date printed: Jul. 28, 2004).
Schessel, Eli S. et al., "External Constant Tension Expansion of Soft Tissue for the Treatment of Ulceration of the Foot and Ankle," *Journal of Foot & Ankle Surgery*, vol. 39, No. 5, pp. 321-328, Sep./Oct. 2000.
Galil, K. et al., "Effect of N-Butyl-2-Cyanoacrylate (Histoacryl Blue) on the Healing of Skin Wounds," *J. Canad. Dent. Assn.*, No. 7, pp. 565-569 (1984).
Gibson, T. et al., "Directional Variation in Extensibility of Human Skin in Vivo," *J. Biomechanics*, vol. 2, pp. 201-204 (1969).
Gibson, T. et al., "The Mobile Micro-Architecture of Dermal Collagen," *Brit. J. Surg..*, vol. 52, No. 10, pp. 764-770 (Oct. 1965).
Hirshowitz, B. et al., "A Skin-Stretching Device for the Harnessing of the Viscoelastic Properties of Skin," *Plastic and Reconstructive Surgery*, vol. 92 No. 2, pp. 260-270 (Aug. 1993).
Liang, M. et al., "Presuturing—A New Technique for Closing Large Skin Defects: Clinical and Experimental Studies," *Plastic and Reconstructive Surgery*, vol. 81, No. 5, pp. 694-702 (May 1988).

(56) References Cited

OTHER PUBLICATIONS

Mustoe, T. et al., "Physical, Biomechanical, Histologic, and Biochemical Effects of Rapid versus Conventional Tissue Expansion," *Plastic and Reconstructive Surgery*, vol. 83, No. 4, pp. 687-691 (Apr. 1989).

Radovan, C., "Tissue Expansion in Soft-Tissue Reconstruction," *Plastic and Reconstructive Surgery*, vol. 74, No. 4, pp. 482-490 (Oct. 1984).

Stark, H. et al., "Directional Variations in the Extensibility of Human Skin," *British Journal of Plastic Surgery*, vol. 30, pp. 105-114 (1977).

\* cited by examiner

WOUND CLOSURE PRODUCT

CROSS REFERENCE TO RELATED APPLICATIONS

This application is a continuation of U.S. patent application Ser. No. 14/511,416, filed Oct. 10, 2014, now U.S. Pat. No. 9,597,079, which is a continuation of U.S. patent application Ser. No. 12/750,353, filed Mar. 30, 2010, now U.S. Pat. No. 8,864,796, which is a continuation of U.S. patent application Ser. No. 10/982,509, filed Nov. 4, 2004, now U.S. Pat. No. 7,686,829, which applications are hereby incorporated by reference in their entirety.

TECHNICAL FIELD

The principles disclosed herein relate generally to wound closure by facilitating stretching of skin tissue. More specifically, the disclosure relates to a system and method of facilitating expanding the skin tissue over a wound by use of dynamic force.

BACKGROUND

Surgical procedures such as tumor removal or fasciotomies can result in large skin wounds. Chronic wounds such as diabetic ulcers frequently do not heal. Techniques have been developed to facilitate the wound closure of large skin defects and chronic wounds.

Common methods for closure of wounds and skin defects include split thickness skin grafting, flap closure and gradual closure utilizing tissue expansion. A split thickness skin graft involves removing a partial layer of skin from a donor site, usually an upper leg or thigh, and leaving the dermis at the donor site to re-epithelialize. In this manner, a viable skin repair patch can be transferred or grafted to cover the wound area. The graft is often meshed, (which involves cutting the skin in a series of rows of offset longitudinal interdigitating cuts) allowing the graft to stretch to cover an area two or three times greater than the wound, as well as provide wound drainage while healing. Normal biological function of the skin heals the cuts after the graft has been accepted. A meshed graft of this type requires a smaller donor area than a conventional non-meshed or full thickness skin graft. Flap closure involves transferring skin from an adjacent region to the wound. This technique is only effective in anatomical regions that are amenable to transfer of adjacent skin. It is also a more complex surgical procedure involving increased surgical costs and risks. Both of these methods do not provide optimal cosmesis or quality of skin cover. Other disadvantages of these methods include pain at the donor site, creation of an additional disfiguring wound, and complications associated with incomplete "take" of the graft. In addition, skin grafting often requires immobilization of the limb, which increases the likelihood of contractures. The additional operation and prolongation of hospital stay is an additional economic burden.

Gradual, or progressive, closure is another method of wound closure. This technique may involve suturing vessel loops to the wound edge and drawing them together with large sutures in a fashion similar to lacing a shoe. In addition, the wound edges may be progressively approximated with suture or sterile paper tape. The advantages of this gradual, or progressive, technique are numerous: no donor site is required for harvest of a graft; limb mobility is maintained; superior cosmetic result, more durable skin coverage, better protection because skin is full thickness, and maintenance of normal skin sensation may all be achieved.

Existing devices for effecting a gradual closure, however, have many disadvantages. Current methods and devices rely on static ribbon or suture material which must be repeatedly readjusted in order to draw wound edges together because a relatively small skin movement substantially eliminates much of the closure force. Even with constant readjustment, maintenance of near constant tension over time is difficult, if not impossible, to achieve. Since widely used existing closure techniques involve use of relatively inelastic materials such as sutures or surgical tape, a substantial amount of tension is put on the wound edges during periodic adjustment to obtain the necessary closure force. Excessive tension may cut the skin or cause necrosis due to point loading of the tissue.

What is needed in the art is a gradual wound closure technique that is self-regulating and self-adjusting and uses continuous or dynamic tension to draw the wound edges together, without obstructing the wound, thus eliminating the need for constant readjustment involved with the static systems.

SUMMARY

The principles disclosed herein relate to wound closure by facilitating stretching of skin tissue. The disclosure relates to a system and method of facilitating expanding the skin tissue over a wound by use of dynamic force.

The disclosure is directed to a wound closure system including components adapted to apply a dynamic tension force on a plurality of anchors that are attached to skin tissue surrounding a wound. The dynamic tension force draws the anchors toward the wound facilitating stretching of the skin tissue over the wound area.

In one particular aspect, the disclosure is directed to a wound closure system comprising a plurality of skin anchors mechanically attached to external skin tissue around a generally linear wound. The skin anchors are configured to pass a line extending between multiple skin anchors across the wound. A single line or multiple lines may be used. Application of tension to the line(s) draws the skin anchors toward each other and toward the wound. The tension is applied by a tensioning apparatus that is mechanically attached to the external skin tissue.

In another particular aspect, the disclosure is directed to a wound closure system comprising a plurality of skin anchors mechanically attached to external skin tissue on opposite sides of a generally linear wound, a line extending between the skin anchors to slidably connect the anchors, the line slidably engaged with at least one skin anchor, and a biasing member that provides tension on the line to draw the connected skin anchors toward each other and toward the wound.

In an alternate embodiment, the disclosure is directed to a wound closure system comprising a skin anchor mechanically attached to external skin tissue on a first side of a generally linear wound, an anchorable tensioning apparatus mechanically attached to external skin tissue on an opposite side of the wound, a line extending between the skin anchor and the tensioning apparatus to movably connect the anchor to the tensioning apparatus, the line fixedly engaged with the anchor, with the tensioning apparatus providing tension on the line to draw the skin anchor and the tensioning apparatus toward each other and toward the wound.

In yet another particular aspect, the disclosure is directed to a method of closing a wound, the method comprising the steps of mechanically attaching a skin anchor to external tissue on a first side of a generally linear wound, mechanically attaching an anchorable tensioning apparatus to external skin on an opposite side of the wound, extending a line between the skin anchor and the tensioning apparatus to movably connect the anchor to the tensioning apparatus, and providing tension to the line to draw the skin anchor and the tensioning apparatus toward each other and toward the wound.

In yet another particular aspect, the disclosure is directed to a wound closure kit comprising a skin anchor adapted for attachment to external skin tissue, a line adapted to be coupled to the skin anchor, an anchorable tensioning apparatus adapted for attachment to external skin tissue and adapted for providing tension on the line.

In yet another particular aspect, the disclosure is directed to an alternative use of the wound closure system where the wound closure system may be used for cosmetic purposes to stretch the skin at certain parts of the body that do not include wounds.

DETAILED DESCRIPTION

The inventive aspects of the disclosure will now be described by reference to the several drawing figures. The functional features of the inventive aspects can be embodied in any number of specific configurations. It will be appreciated, however, that the illustrated embodiments are provided for descriptive purposes and should not be used to limit the inventions described herein.

A. Wound Closure System

Figure 1:
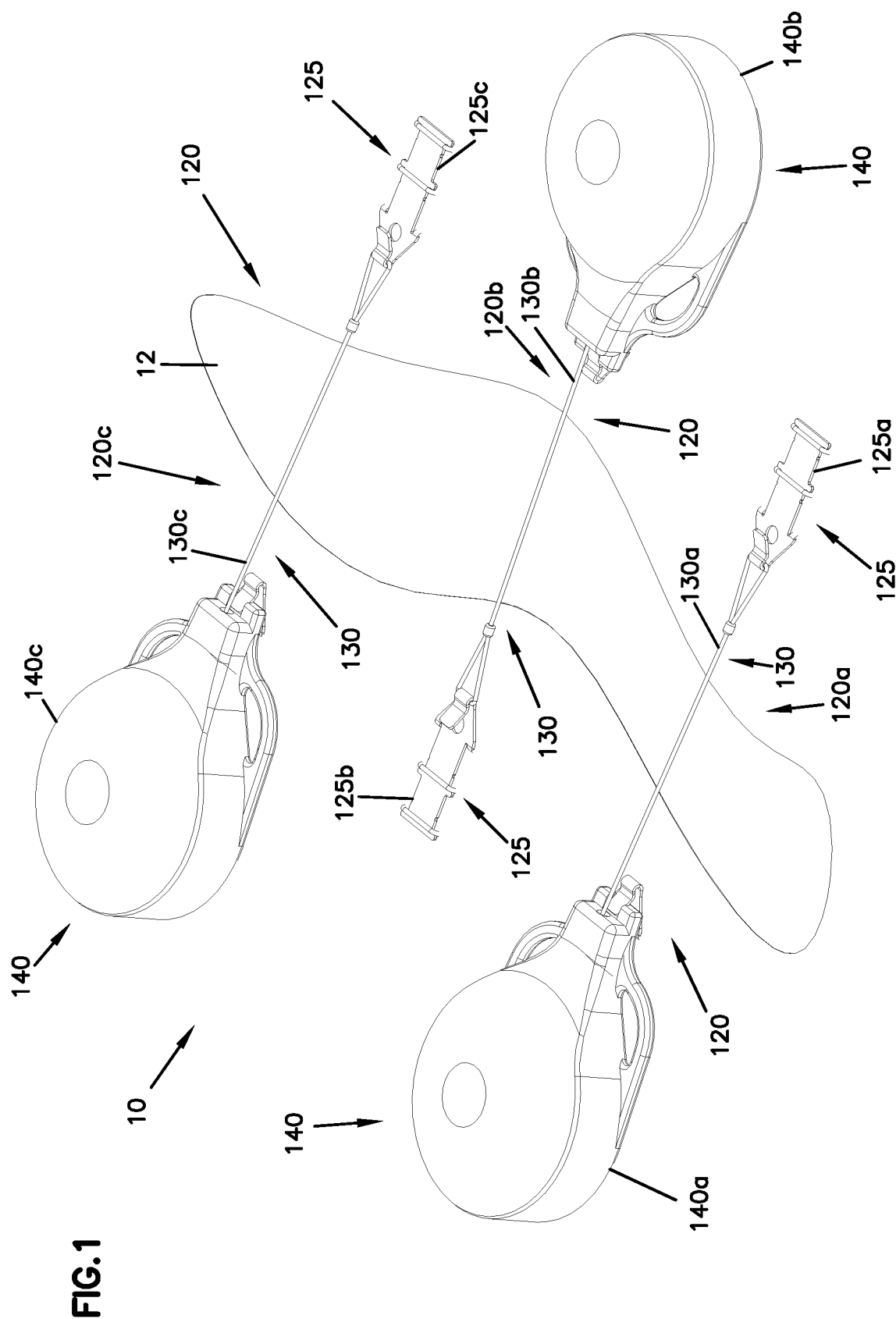
FIG. 1 is a top perspective view of a wound closure system in accordance with the principles of the present disclosure, illustrating multiple stretching elements operably positioned in relation to a wound.

FIG. 1 illustrates a wound closure system 10 having features that are examples of inventive aspects disclosed herein. The wound closure system 10 illustrated in FIG. 1 includes a plurality of stretching elements 120 (each individually indicated as 120a, 120b and 120c) generally positioned around the periphery of a wound 12. Elements 120a, 120b, 120c, etc. are attached to the skin surrounding wound 12 by mechanical means (e.g., staples). Each element 120 includes an anchor 125 (each individually indicated as 125a, 125b, 125c) and an anchorable tensioning apparatus 140 (each individually indicated as 140a, 140b, 140c). Anchors 125a, 125b, 125c are connected to anchorable tensioning apparatus 140a, 140b, 140c by a tension line 130 (individually indicated as 130a, 130b, 130c).

Figure 2:
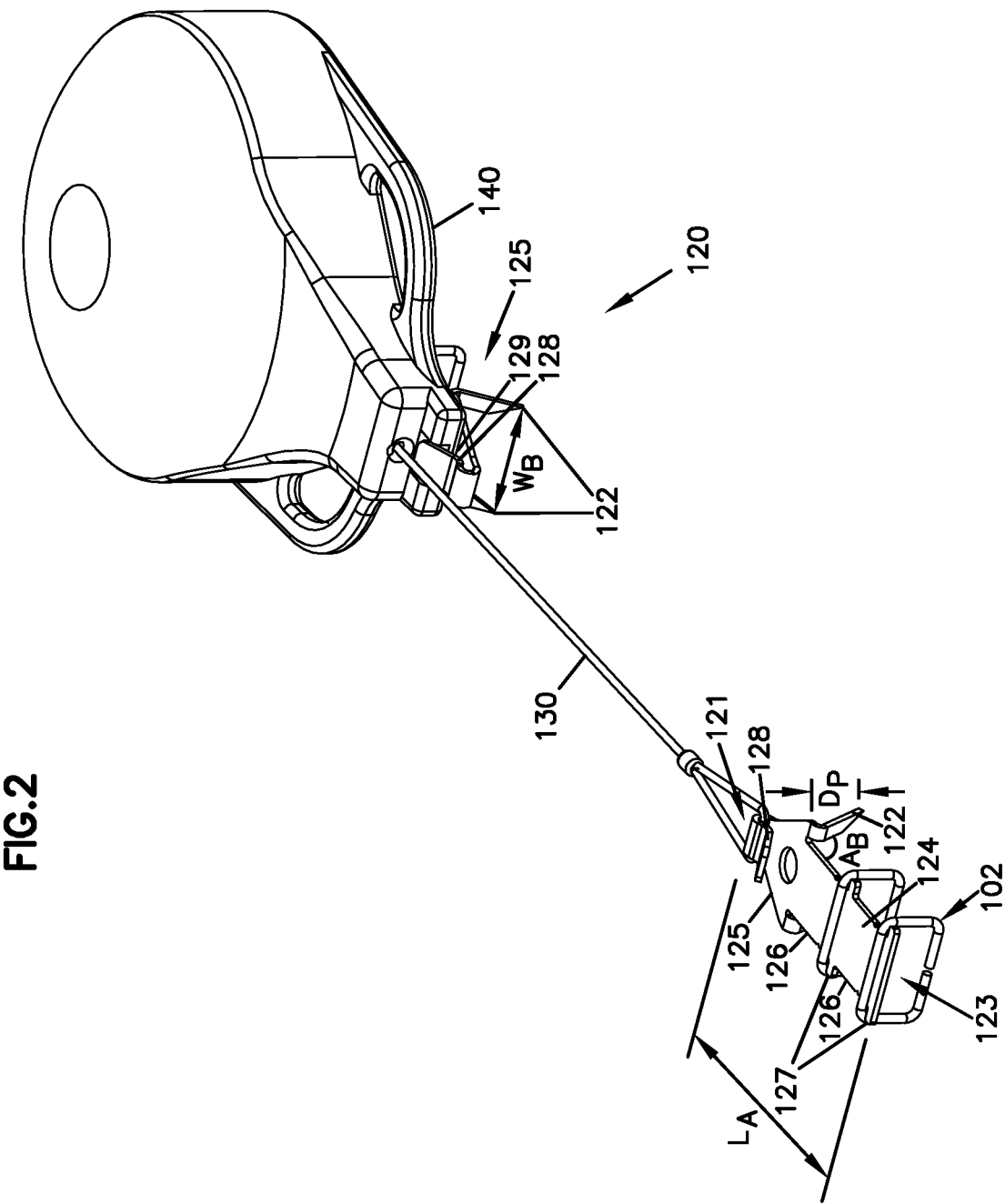
FIG. 2 is a top perspective view of one stretching element of FIG. 1 illustrated alone, the stretching element having a skin anchor and an anchorable tensioning apparatus.

A single stretching element 120, having anchor 125, line 130 and anchorable tensioning apparatus 140, is illustrated in FIG. 2. For ease of understanding, the inventive aspects of the following disclosure will be described with reference to only a single stretching element, it being understood that multiple elements can be utilized for the wound closure system within the spirit of the invention, as illustrated in FIG. 1.

Referring to FIG. 2, anchor 125 is connected to anchorable tensioning apparatus 140 by tension line 130, which is fixedly attached to anchor 125 and to tensioning apparatus 140 in a manner as to extend across wound 12 (as illustrated in FIG. 1). Anchorable tensioning apparatus 140, which is attached to skin at the opposite side of the anchor 125, is adapted to apply tension to line 130 to draw anchor 125 and the tensioning apparatus 140 inwardly toward each other, and, thus, the skin over the wound. Anchor 125 and tensioning apparatus 140 are positioned to generally linearly move toward each other.

An inelastic or non-stretchable line 130 is preferably used to draw skin anchor 125 and the tensioning apparatus 140 toward wound 12 since the tensioning apparatus 140 is adapted to provide the dynamic force needed for wound closure. An elastic line 130 can also be used, and may be preferred in some embodiments due to its ability to provide lessened tension and more flexibility.

In an alternate embodiment that is within the scope of this disclosure, an elastic line 130 alone that is fixedly attached to two anchors located on opposite sides of a wound can be used to provide the dynamic tension on the skin, without the use of a tensioning apparatus.

B. Anchorable Tensioning Apparatus

Figure 3:
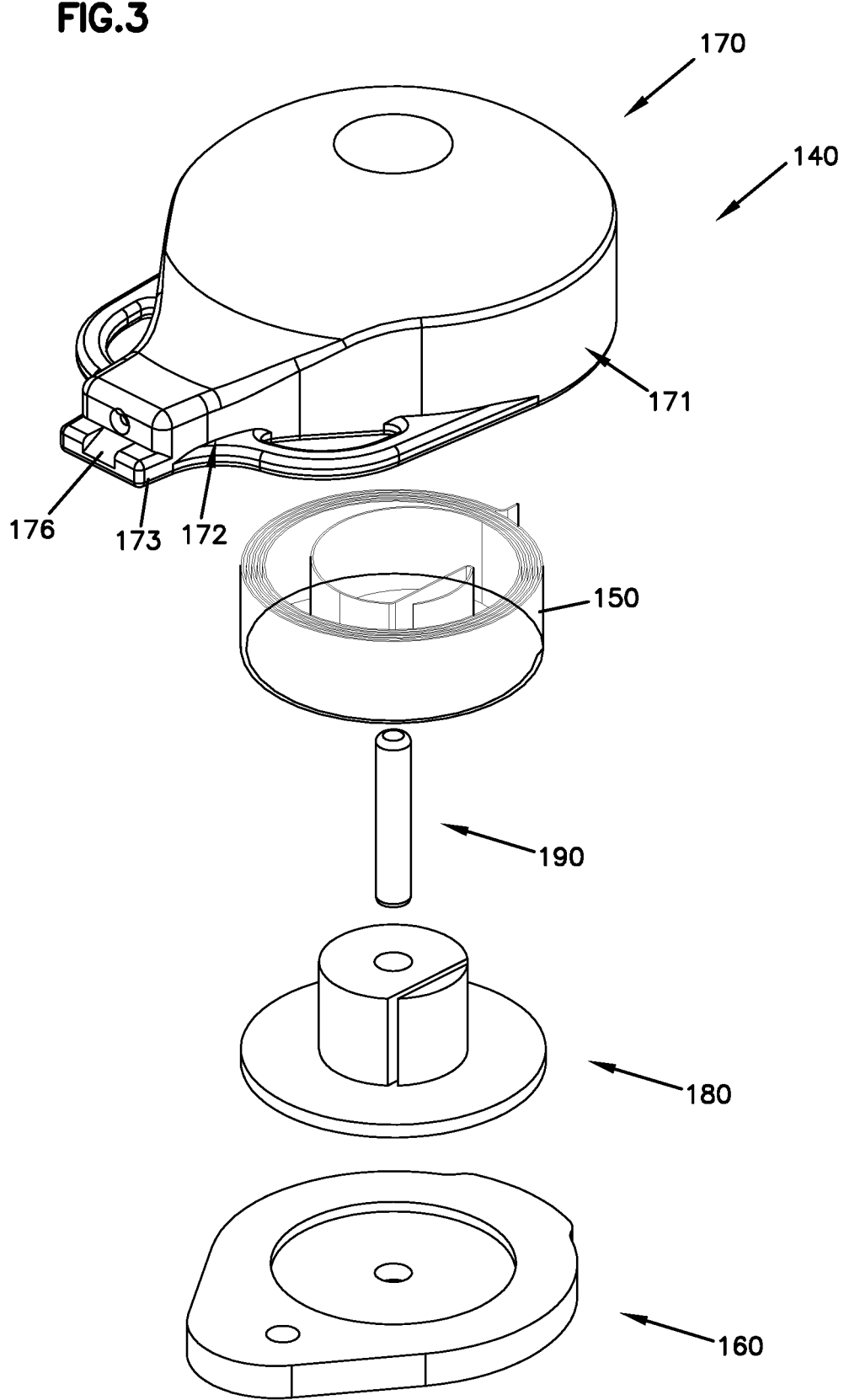
FIG. 3 is an exploded view of the tensioning apparatus of the stretching element of FIG. 2.

Referring to FIG. 3, tensioning apparatus 140 includes a base 160, a spool 180 that seats on the base 160, a biasing member 150 that is placed around the spool 180, a connection rod 190 that extends axially through the tensioning apparatus 140, and a cover 170 that is placed on the base 160 to enclose the individual components of the tensioning apparatus 140.

Figure 4:
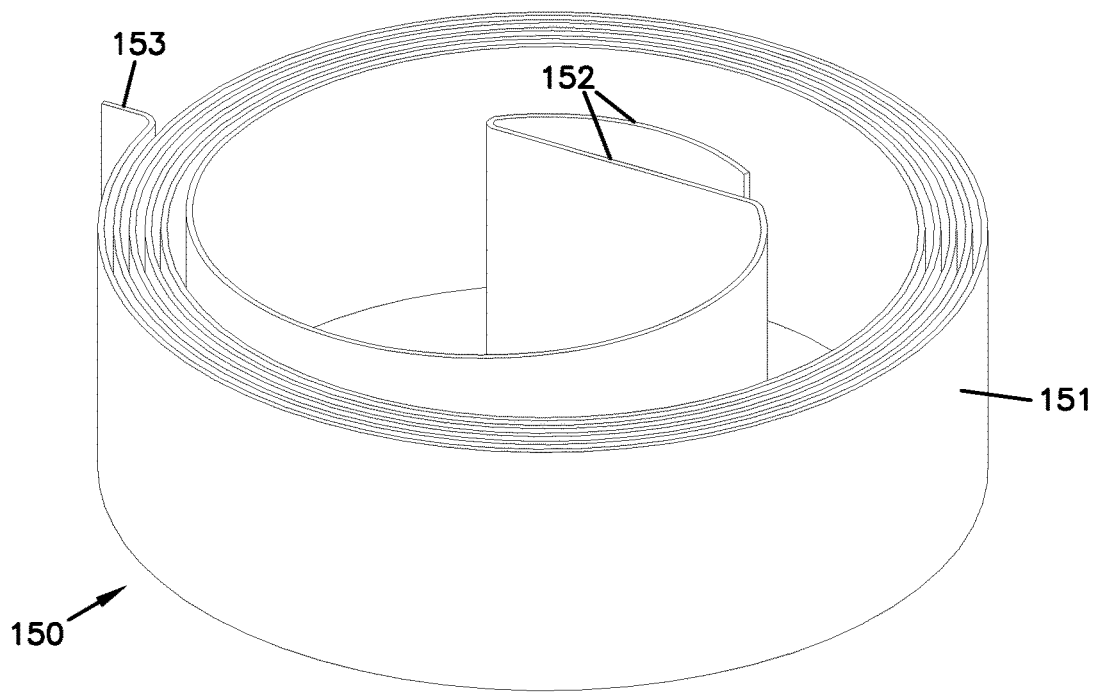
FIG. 4 is an enlarged top perspective view of a biasing member of the tensioning apparatus of FIG. 3.

Referring to FIG. 4, there is generally illustrated therein an enlarged view of the biasing member 150 of the tensioning apparatus 140. The biasing member 150 is adapted to be mounted within tensioning apparatus 140 to provide the dynamic tension force on the skin anchor 125. As the skin stretches and grows over wound 12, anchor 125 moves toward apparatus 140 and toward wound 12, reducing the tension on line 130 and creating "slack" on tension line 130. Biasing member 150 provides the tension to take up the slack on line 130. In certain embodiments, the tension force that is applied to each skin anchor 125 is usually at least 1 oz. and usually no greater than 64 oz., commonly between 4 and 16 oz.

The biasing member 150 is depicted essentially as a spring formed from a coiled-up metal band 151. Although depicted as a coiled spring in FIGS. 3 and 4, biasing member 150 may include other structures. For example, biasing member 150 may include a constant-force spring designed to provide a constant level of tension on line 130 when it is in a loaded state. Biasing member 150 may alternatively include a nonconstant-force spring designed to provide varying amounts of force on line 130 depending upon how tightly it is wound. As one skilled in the art will appreciate, the force application characteristics of such springs depend upon factors such as the mechanical properties of the springs, the thickness, the diameter, etc.

It will be understood that biasing member may also refer to an elastic tension line that is extended across the wound and coupled to two skin anchors on opposite sides of the wound that is used to draw the anchors toward each other and toward the wound.

The band 151 defines an inner hook portion 152 and an outer tab portion 153. The coiled up band 151 is positioned around an upper spring mount portion 182 of the spool 180 (see FIGS. 5A-5C) as will be discussed further below. When positioned as such, a portion of the hook portion 152 of the band 151 is placed within a slot 188 defined on the upper spring mount 182 of the spool 180. The outer tab 153 of the band 151 cooperates with the cover 170 of the tensioning apparatus 140 to stay fixedly in a wound orientation.

Figure 5A:
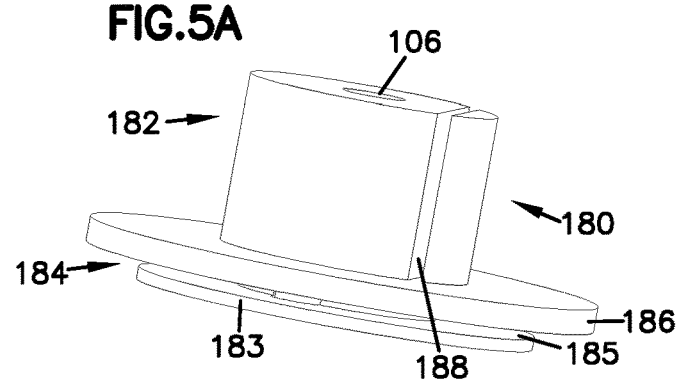
FIG. 5A is a top perspective view of a spool of the tensioning apparatus of FIG. 3.
Figure 5C:
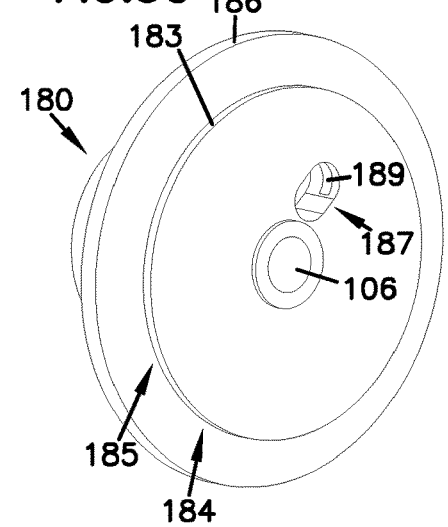
FIG. 5C is another bottom perspective view of the spool of FIG. 5A.
Figure 5B:
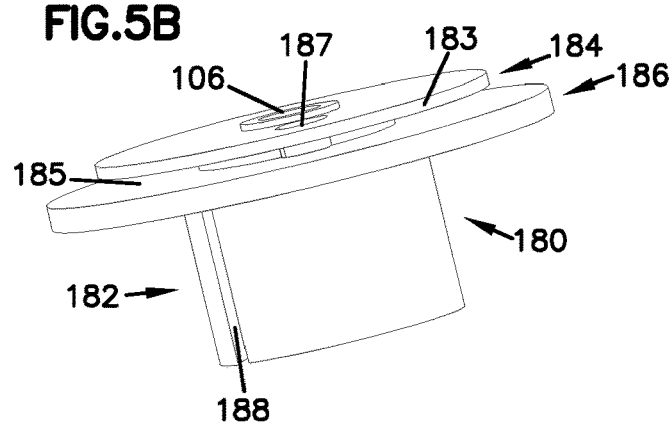
FIG. 5B is a bottom perspective view of the spool of FIG. 5A.

Referring to FIGS. 5A-5C, there is generally illustrated the spool 180 of the tensioning apparatus 140. The spool 180 includes an upper spring mount portion 182, a lower tension line mount portion 184, and a main plate 186 separating the two portions. In this embodiment, all the portions of the spool 180 are depicted as integrally formed from one unitary piece. However, it will be appreciated that in other embodiments, the spool may be formed from multiple separate pieces that are coupled together.

The upper spring mount portion 182 has a generally cylindrical shape. The upper mount portion 182 includes a slot 188 adapted to receive the hook portion 152 of the biasing member 150 as discussed above. The spool 180 also includes a throughhole 106 for receiving the connection rod 190 used to couple the spool 180 to the base 160 of the tensioning apparatus 140.

The lower tension line mount portion 184 defines a winding groove 185. The winding groove 185 is defined between the main plate 186 and a lower seat plate 183. The lower seat plate 183 provides structure for seating the spool 180 into the base 160 of the tensioning apparatus 140. The spool 180 also defines a line attachment hole 187 that communicates with the winding groove 185 through a slit 189 defined within the winding groove 185. Before being wound, one end of the tension line 130 is fed through the slit 189 into the hole 187 and a knot is tied to secure one end of the tension line 130 to the spool 180, the knot being large enough that the end of the line 130 will not slip through the slit 189. After being secured to the spool 180, line 130 is wound around the spool 180 within the winding groove 185.

Figure 6:
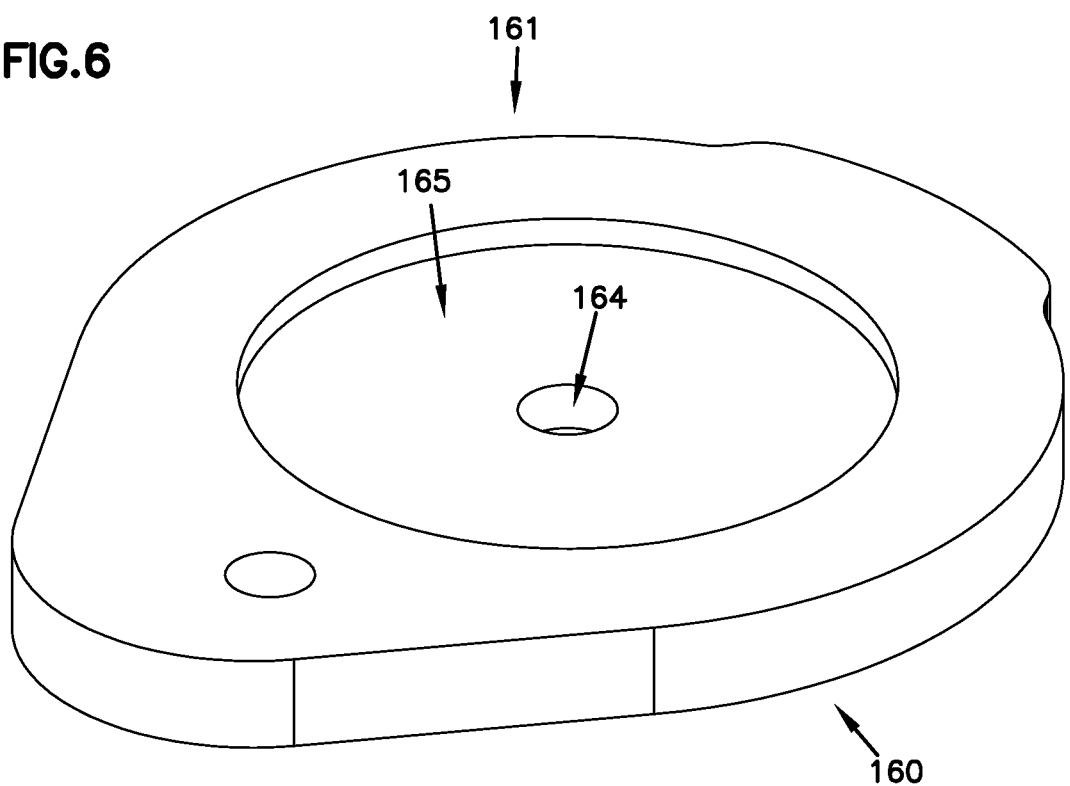
FIG. 6 is an enlarged top perspective view of a base of the tensioning apparatus of FIG. 3.

Referring to FIG. 6, there is generally illustrated the base 160 of the tensioning apparatus 140. Base 160 includes a generally circular main body 161. Defined within the body 161 is an interior cavity 165 shaped to receive the lower seat plate 183 of the spool 180. The base 160 includes a hole 164 defined within the interior cavity 165 for receiving the connection rod 190 used to couple the spool 180 to the base 160.

Referring back to FIG. 3, there is generally illustrated therein the cover 170 of the tensioning apparatus 140. The cover 170 generally includes an interior shape configured to fit around the exterior of the base 160. The cover 170 includes a main body portion 171 and an elongate snout portion 172. The main body portion 171 fits over the main body portion 161 of the base 160.

The interior of the cover 170 (not shown in the FIGS.) is generally shaped and sized to receive the biasing member 150. The interior of the cover 170 includes structure (not shown in the FIGS.) that cooperates with the outer tab portion 153 of the biasing member 150 to keep the biasing member wound up within the cover 170.

The snout portion 172 of the cover 170 includes a hole for feeding an end of the tension line 130 out of the cover 170, the other end of the tension line having been attached to the spool 180 located within the cover 170. The front of the snout portion 172 includes an extended lip 175 which defines a ramped surface 176. The ramped surface 176 is configured to cooperate with a tension line tab 128 of a skin anchor 125 to fixedly mount the cover 170 to a skin anchor 125. As shown in FIG. 3, the ramped surface 176 is inserted within a tension line slot 129 defined by the tension line tab 128 of the skin anchor 125 as the tension line tab 128 abuts against the front of the snout 172. With this feature, the tensioning apparatus 140 can be allowed to move with the anchor 125 as the skin is stretched toward the wound 12.

It will be appreciated that, although the tensioning apparatus is depicted as a unit that is separate from the skin anchor that it is attached to, the tensioning apparatus may include an integrally formed anchoring means adapted to anchor the tensioning apparatus to external skin.

C. Skin Anchors

As seen in FIG. 1, anchors 125a, 125b, 125c are placed around the periphery of wound 12. Each anchor 125 is mechanically fastened to the skin, such as by conventional medical skin staples. Suturing can also be used to mechanically attach anchors 125 to the skin.

Referring to FIG. 2, two skin anchors 125 of the stretching element 120 are generally illustrated therein. Each anchor 125 includes a first end 121, a second opposite end 123, and a generally rectangular body 124 defined between the first end 121 and the second end 123. The anchor 125 includes two skin-penetrating barbs 122 proximate the first end 121 for securement to the skin. The barbs 122 preferably have a bearing surface with a large enough width perpendicular to the direction of the tension so that the barbs 122 do not cut through the skin when pulled toward the wound 12 in tension. In this manner, as the barbs 122 move in toward the wound, the skin moves with the barbs 122. The barbs 122 can be bent at an angle $A_B$ less than about 90 degrees from the skin surface. The barbs 122 can be bent, preferably, at about a 60-degree angle $A_B$ to improve their ability to hold into the skin. The edges of the barbs 122 are sharp to make it easy to penetrate the skin upon insertion. Two pairs of indentations, generally indicated at 126, are formed on opposite sides of the body 124 of the anchors to help guide where mechanical attachment, such as staples 102, are to be placed. Two pairs of tabs 127 extending out from the opposing sides of the body 124 are adapted to abut against the staples 102 to pull the skin toward wound 12. Although the guiding indentations 126 are located forward of the tabs 127, as anchor 125 is pulled in toward wound 12, the tabs 127 eventually abut against the staples 102 after initial stretching of the skin around the wound area is achieved.

The tension line tab 128 defines the tension line slot 129 formed at the first end 121 of the anchor 125 for receiving tension line 130. The tension line slot 129 is formed with a wide lead-in area to make it easy to receive tension line 130. The tension line slot 129 may be sized such that tension line 130 is "snapped-in" past the narrowest point of the slot 129 to prevent the line from accidentally being pulled out.

Still referring to FIG. 2, anchor 125 includes a length $L_A$. The barbs 122 include a penetration depth $D_P$. The inner edges of the barbs 122 are spaced apart a distance of $W_B$. The dimensions, $L_A$, $D_P$, $W_B$, and $A_B$ can be varied according to desired skin anchor performance in different parts of the human body and for different types and ages of skin.

Table 1, below, illustrates two example configurations for the anchor, with two different sets of dimensions that are suitable for use with the stretching element 120. Anchors with example configuration 1 are preferably retained by two conventional regular size medical skin staples (5.7 mm×3.9 mm). Anchors with example configuration 2 are preferably retained by two wide size medical skin staples (6.9 mm×3.9 mm).

TABLE 1

Anchors (unless otherwise specified, all dimensions are in inches)

|  | $L_A$ | $D_P$ | $W_B$ | $A_B$ |
| --- | --- | --- | --- | --- |
| Configuration 1 | 0.739 | 0.158 | 0.186 | 60° |
| Configuration 2 | 0.607 | 0.115 | 0.206 | 60° |

In a preferred embodiment, the anchor 125 is formed from stainless steel sheet such as 302 or 316 containing 8 to 14% nickel content. It will be appreciated that the anchors can be stamped with a progressive die, wire EDM-cut, shaped from metal, shaped from wire, injection molded, or made by other suitable methods. The anchors can also be manufactured from other metals such as titanium.

The barbs of the skin anchors described above could optionally include a hollow portion and an exit hole or aperture adapted to be exposed to the undersurface of the skin once the barb penetrates the skin. A medicinal component, such as anesthesia (such as "Lidocaine") or an antibacterial material, may be applied through the hole and thus to the skin. Any such medicinal component may be provided by a continuous source, such as by being connected to an IV drip, or be applied when the anchor is attached to the skin. In this manner, the medicinal component can be supplied around wound area 12 through skin punctures that have been created by the barbs of the skin anchors.

D. Tension Line

Referring back to FIG. 1, tension line 130 of stretching element 120 is illustrated as being coupled to anchor 125 across wound 12. Suitable examples for tension line 130 include nylon or polypropylene line, suture material, string, a cable, a wire, or other similar item. Line 130 should be sufficiently flexible and bendable to allow attachment to anchor 125. In a preferred embodiment, tension line 130 is conventional suture material. One preferred line 130 is made from nylon and has a tensile strength of about 6 lbs to 10 lbs. Tension line 130 preferably includes a thread diameter of about 0.5 mm to 0.6 mm.

Although depicted as including a separate tensioning apparatus in FIGS. 1 and 2, the stretching element 120 may instead utilize a line 130 that includes elastic material to provide the dynamic tension on skin anchors 125. This elastic line may also be referred to as a biasing member that provides the tension needed to pull the anchors toward each other and the wound. With the use of a tensioning apparatus such as 140, however, an inelastic line can be utilized to draw skin anchors 125 toward wound 12 since the tensioning apparatus is adapted to provide the dynamic force needed for wound closure. An elastic line can also be used in addition to a separate tensioning apparatus.

E. General Use of Wound Closure System

General assembly and use of the system will be described with reference to FIGS. 2 and 3. In general use, first, the skin anchors 125 are placed at the opposing sides of a generally linear wound (see FIG. 1 for wound 12). After penetrating the skin by pressing the skin engagement barbs 122 of the anchors 125 into the skin, skin anchors 125 may then be further coupled to the skin with the use of, for example, staples 102. The two pairs of indentations 126 defined on the body 124 of skin anchor 125 serve as target areas for placement of the staples 102.

After one end of the tension line 130 has been secured to the spool 180 and the line wound around the spool, the tensioning mechanism 140 may be assembled with the spool 180 fitting into the base 160. The free end of the line 130 is guided out of the snout portion 172 of the cover 170. The biasing member 150 is placed on top of the spool 180, and the cover 170 is mounted on top of the base 160 enclosing the tensioning apparatus 140.

After assembly of the tensioning apparatus 140, a loop is tied at the free end of the line 130 that is fed out of the snout portion 172 of the cover 170. The loop is placed around the tension line tab 128 of the anchor 125 on one side of the wound. Then, the tensioning apparatus 140 may be pulled across the wound and attached to the anchor at the opposite side of the wound, with the biasing member 150 in a wound-up orientation. As anchors 125 move in toward each other and toward the wound by the stretching of the skin, the wound-up biasing member 150 and hence the spool 180 keeps line 130 taut. As mentioned above, depending on the size and shape of the wound, one or more stretching elements may be utilized as part of the wound closure system.

The tensioning apparatus 140 may be easily removed from the anchor 125 by holding the line 130 and pulling the tensioning apparatus back away from the anchor to which it is attached.

F. Alternative Embodiment of Wound Closure System

Figure 7:
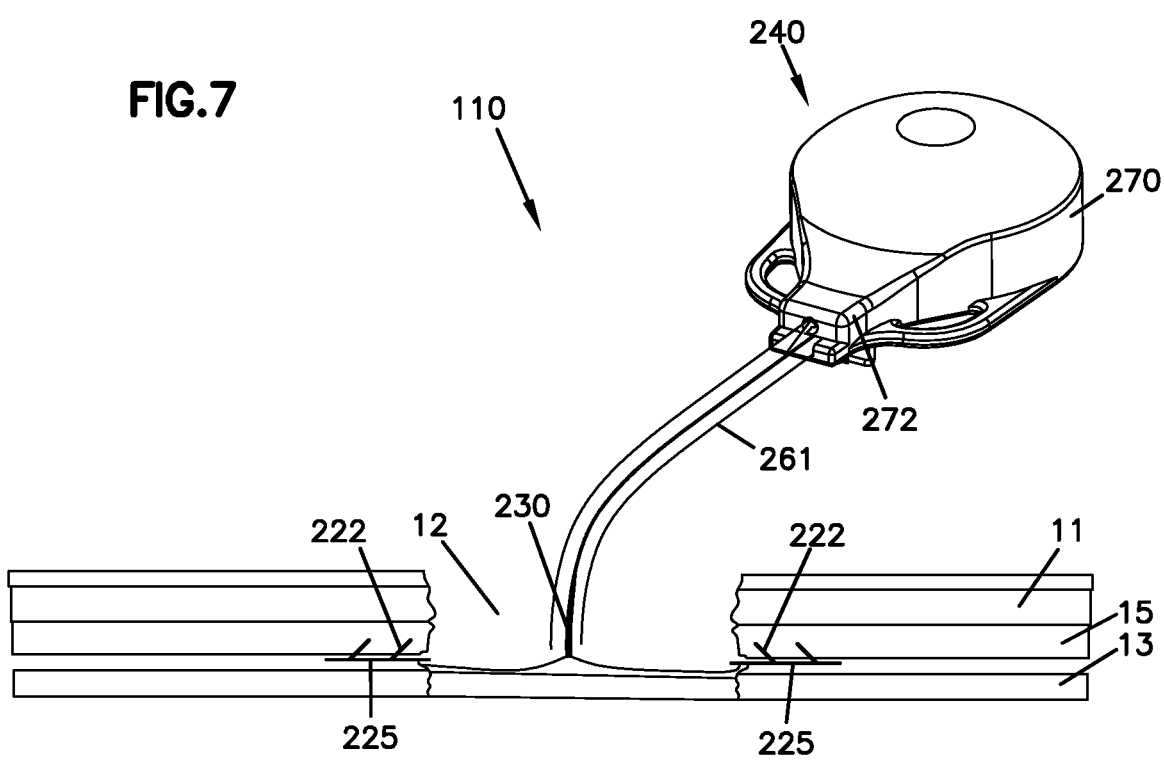
FIG. 7 is a top perspective view of an alternative embodiment of a wound closure system in accordance with the principles of the present disclosure, the wound closure system illustrated in combination with a cross-sectional view of the skin.

Referring to FIG. 7, in an alternate configuration of a wound closure system 110 according to the present disclosure, skin anchors 225 (including features similar to anchors 125 of FIGS. 1 and 2) can be placed under the dermis 11. In the configuration of the wound closure system 110, the edges of a wound, such as wound 12, would be undermined and then the skin anchors 225 would be inserted between the muscle layer 13 and the subcutaneous fat layer 15. A line 230 from a tensioning apparatus 240 (line 230 and tensioning apparatus 240 including features similar to line 130 and tensioning apparatus 140 described above, respectively) would be attached to the skin anchors 225. The tensioning apparatus may include a rigid conduit 261 through which line 230 may pass, the conduit 261 running from a snout portion 272 of a cover 270 of the tensioning apparatus 240 to the middle of the wound 12. The rigid conduit 261 may be similar to a force guide tube disclosed in U.S. Pat. No. 7,455,681, the disclosure of which is incorporated herein in its entirety. The rigid conduit 261 provides structural support for the line 230 and allows the tensioning apparatus 240 to be positioned at a remote location from the wound 12. The rigid conduit provides a way to concentrate the pulling force of the tensioning apparatus 240 into a single point at the center of the wound 12.

The sub-dermal skin anchors 225 may be made from any suitable material and may include features similar to skin anchors 125. A preferred design is to have the skin anchor 225 made from stainless steel and having four skin engagement barbs 222 bent at an angle, such as 60 degrees.

In general use, to insert the skin anchors 225, the physician would undermine the skin along the edge of the wound 12. The subcutaneous fat layer 15 would be spread from the muscle layer 13 and the skin anchor 225 would be inserted therebetween. The skin engagement barbs 222 would then engage into the subcutaneous fat 15 and the dermis 11. The skin engagement barbs 222 are preferably angled so that as more force is applied to the tension line 230, the anchors 225 are pulled further into the dermis 11.

In another embodiment of the skin anchors, the skin engagement barbs can be configured to pivot. The barbs could be configured such that the barbs would go from a flat position to an angled position via a pivoting structure such as a hinge. When first inserted into the skin, the skin engagement barbs would be flat or parallel to the surface of the skin anchors and as the anchors are pulled toward the wound by the tensioning apparatus 240, the barbs would pivot up and start penetrating the subcutaneous fat layer 15 and the dermis 11. An advantage of this design would be that it would not be necessary to spread the subcutaneous fat layer 15 from the muscle layer 13 as the skin anchors would be easy to slide in between the two layers. When tension is applied to the tension line 230, the skin engagement barbs would pivot until a stop position is encountered. This stopping position could be provided at such a point that an angle of 60 degrees or a similar angle from parallel is achieved. The skin engagement barbs would then dig into the dermis and start stretching the skin as force is applied to the tension line 230.

In another embodiment of the sub-dermal skin anchors, the skin anchors could be made from an absorbable material, that is, a material that is absorbed by body fluids. Such a design has the advantage of not needing to remove the skin anchors after the skin has stretched adequately to close the wound. The anchors would just be left under the dermis and gradually dissolve.

It should be appreciated that the wound closure system 110 utilizing sub-dermal skin anchors 225 can be used with a linear wound closure system such as one described in the present disclosure or could be used with a radial wound closure system such as one described in the pending patent application U.S. Pat. No. 7,455,681. In a linear system, the line 230 coming out of the tensioning apparatus 240 would be split into two ends, each end being coupled to opposing skin anchors 225 to draw the skin anchors toward each other. In a radial system, a single line in the form of a loop can be coupled to anchors placed around the wound as described in further detail in U.S. Pat. No. 7,455,681.

G. Alternative Use of Wound Closure System

The wound closure system may be used to stretch the skin for purposes other than for wound closure. One such example use of the wound closure system is directed to improving the cosmetic effects of male-pattern baldness. For example, the skin anchors may be placed on the human scalp such that the tension line extends across the so called "bald spot." The tensioning apparatus or an elastic tension line, for example, then may be used to gradually draw the skin anchors toward each other to stretch the skin with the hair follicles surrounding the bald spot to eventually reduce the size of the bald spot.

From the foregoing detailed description, it will be evident that modifications and variations can be made in the devices of the invention without departing from the spirit or scope of the invention. Therefore, it is intended that all modifications and variations not departing from the spirit of the invention come within the scope of the claims and their equivalents.

We claim:

1. A wound closure system comprising:
   (a) a skin anchor configured to be mechanically attached to external skin tissue on a first side of a wound; wherein the skin anchor is configured to be attached to skin tissue with a skin-penetrating barbs;
   (b) an anchorable tensioning apparatus configured to be attached to external tissue on an opposite second side of the wound and outside a periphery of the wound, wherein the tensioning apparatus includes a spool attached to a wound coil spring and the wound coil spring is a coiled-up band placed around the spool; and
   (c) a line configured to extend between the skin anchor and the tensioning apparatus across the wound and above the wound along the entire length of the line, wherein the line is configured to wind around the spool;
   (d) wherein the tensioning apparatus is configured to provide tension via the wound coil spring on the line to draw the skin anchor and the tensioning apparatus toward each other.

2. A wound closure system according to claim 1, wherein the line is inelastic.

3. A wound closure system according to claim 1, wherein the tensioning apparatus provides continuous tension to the line via unwinding of the wound coil spring.

4. A wound closure system according to claim 3, wherein a portion of the line is wound around the spool, and wherein the tensioning apparatus includes a base and a cover that cooperatively house and enclose the spool, the portion of the line wound around the spool, and the wound coil spring.

5. A wound closure system according to claim 1, wherein the wound coil spring is one of a constant-force spring and a nonconstant-force spring.

6. A wound closure system according to claim 1, wherein the tensioning apparatus includes a base and a cover, and wherein the band includes an outer tab that is configured to cooperate with the cover to stay fixedly in a wound orientation.

7. A wound closure system according to claim 1, wherein each skin anchor includes at least two skin-penetrating barbs.

8. A wound closure system according to claim 1, wherein the line is suture material.

9. A wound closure system according to claim 1, further comprising a plurality of skin anchors, a plurality of tensioning apparatuses, and a plurality of lines.

10. A wound closure kit comprising:
    (a) a skin anchor configured for attachment to external skin tissue; wherein the skin anchor is configured to be attached to skin tissue with a skin-penetrating barbs;
    (b) an anchorable tensioning apparatus configured for attachment to external skin tissue on an opposite side of a wound as the skin anchor and outside a periphery of the wound, the anchorable tensioning apparatus configured to provide dynamic tension to draw the skin anchor toward the tensioning apparatus, wherein the tensioning apparatus includes a spool attached to a wound coil spring and the wound coil spring is a coiled-up band placed around the spool; and
    (c) a line configured to couple the skin anchor to the tensioning apparatus such that the line extends across the wound and above the wound along the entire length of the line, and wherein the line is configured to wind around the spool.

11. A wound closure kit according to claim 10, wherein the skin anchor is a first skin anchor and the wound closure kit further comprising a second skin anchor configured for attachment to external skin tissue on the opposite side of the wound as the skin anchor, and wherein the anchorable tensioning apparatus is removably attached to the second skin anchor.

12. A wound closure kit according to claim 10, wherein the skin anchor is configured for attachment on a first side of a wound, wherein the anchorable tensioning apparatus is configured for attachment on a second side of the wound, opposite the first side, and outside the periphery of the wound, and wherein the spool is configured such that the spool defines a winding axis that is generally perpendicular to a surface of the external skin tissue at the second side when the tensioning apparatus is attached to the external skin tissue at the second side of the wound.

13. A wound closure kit according to claim 10, wherein once the coil spring is wound by a user, the coil spring of the tensioning apparatus is configured to automatically unwind to rotate the spool to provide continuous tension on the line to draw the skin anchor and the tensioning apparatus toward each other.

* * * * *